United States Patent
Dugand et al.

(10) Patent No.: US 10,145,800 B1
(45) Date of Patent: Dec. 4, 2018

(54) METHOD FOR DETECTING CORROSION OF A SURFACE NOT EXPOSED TO VIEW OF A METAL PIECE, BY MEANS OF THERMOGRAPHIC ANALYSIS

(71) Applicant: C.R.F. Società Consortile per Azioni, Orbassano (Turin) (IT)

(72) Inventors: Marie Marguerite Dugand, Orbassano (IT); Claudio Errigo, Orbassano (IT)

(73) Assignee: C.R.F. Società Consortile per Azioni, Orbassano (Turin) (IT)

( * ) Notice: Subject to any disclaimer, the term of this patent is extended or adjusted under 35 U.S.C. 154(b) by 0 days.

(21) Appl. No.: 15/987,376

(22) Filed: May 23, 2018

(30) Foreign Application Priority Data

May 24, 2017 (EP) ..................... 17172671

(51) Int. Cl.
*G01N 21/88* (2006.01)
*G01N 21/71* (2006.01)
*G01J 5/10* (2006.01)
*G01J 5/00* (2006.01)

(52) U.S. Cl.
CPC ............... *G01N 21/71* (2013.01); *G01J 5/10* (2013.01); *G01N 21/88* (2013.01); *G01J 2005/0077* (2013.01); *G01J 2005/0085* (2013.01)

(58) Field of Classification Search
CPC ....... G01J 2005/0077; G01J 2005/0085; G01J 5/10; G01N 21/71; G01N 21/88
See application file for complete search history.

(56) References Cited

U.S. PATENT DOCUMENTS

| 3,808,439 A | 4/1974 | Renius |
| 5,376,793 A | 12/1994 | Lesniak |
| 5,874,309 A * | 2/1999 | Chang .................. G01N 17/006 436/1 |

(Continued)

FOREIGN PATENT DOCUMENTS

| DE | 10 2010 023 655 A1 | 12/2011 | |
| WO | WO-2009007395 A1 * | 1/2009 | ........... G01N 17/006 |

OTHER PUBLICATIONS

Endo, Hideki et al., "Efficient Inspection for Gas Pipes by Infrared Thermoggraphy", Kobelco Technology Review No. 33, p. 50-55 (Feb. 1, 2015).

(Continued)

*Primary Examiner* — Mark R Gaworecki
(74) *Attorney, Agent, or Firm* — RMCK Law Group PLC

(57) ABSTRACT

In a method for detecting corrosion of a surface not exposed to view of a metal piece, radiant thermal energy is directed against the piece by pulsed laser beam illumination thereby causing heating of said piece. Infrared radiation emitted by the piece is detected by a thermographic camera so that corroded portions of said surface are detected due to a different thermal response as a function of time relative to non-corroded portions. The laser beam is directed against an exposed face of a wall of said piece whose opposite face is the surface on which corrosion must be detected. The thermographic camera is provided on a same side where a laser head for emitting said laser beam is provided and has a control system for performing "Lock-in" thermography. Detection of the surface corroded portions is carried out by comparing a response of different surface portions during cooling of the piece.

2 Claims, 2 Drawing Sheets

(56) References Cited

U.S. PATENT DOCUMENTS

Figure 1:
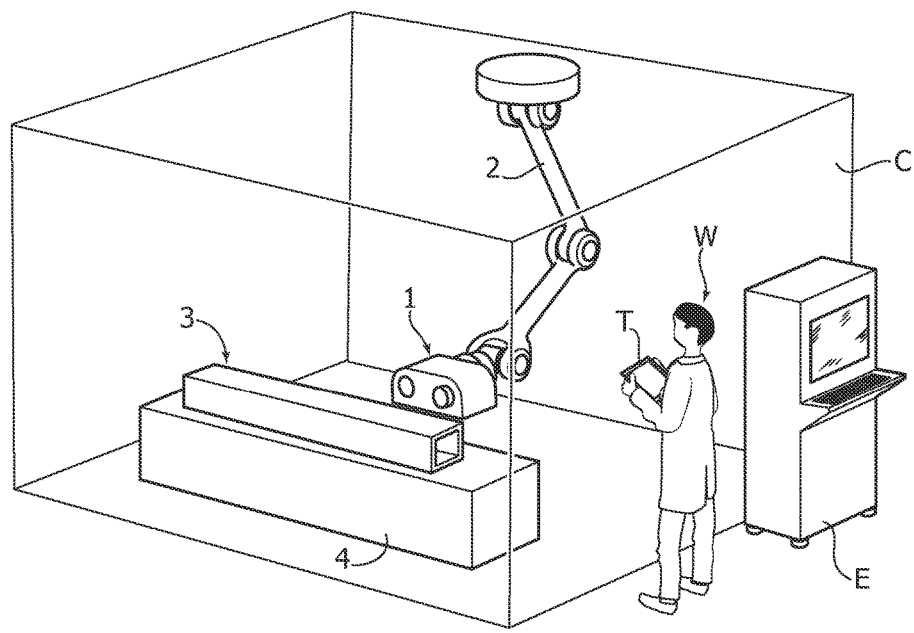

| | | | | |
|---|---|---|---|---|
| 7,220,966 | B2* | 5/2007 | Saito | G01N 25/72 |
| | | | | 250/341.6 |
| 8,204,294 | B2* | 6/2012 | Alloo | G01N 25/72 |
| | | | | 382/141 |
| 2005/0098728 | A1* | 5/2005 | Alfano | G01N 21/3581 |
| | | | | 250/341.8 |
| 2013/0142213 | A1* | 6/2013 | Barberon | G01N 25/72 |
| | | | | 374/5 |

OTHER PUBLICATIONS

Kim, Ju Hyun et al., "On-Power Detection of Pipe Wall-Thinned Defects Using IR Thermography in NPPS", Nuclear Engineering and Technology, vol. 46, No. 2, p. 225-234 (Apr. 1, 2014).

Kim, K.S et al., "Defect detection of pipes using shearography and lock-in infrared thermography", 10th International Conference on Quantitative InfraRed Thermography (Jul. 27-30, 2010).

European Search Report dated Oct. 9, 2017 for EP 17172671.4, 4 pages.

* cited by examiner

METHOD FOR DETECTING CORROSION OF A SURFACE NOT EXPOSED TO VIEW OF A METAL PIECE, BY MEANS OF THERMOGRAPHIC ANALYSIS

CROSS-REFERENCE TO RELATED APPLICATION

This application claims priority to European Patent Application No. 17 172 671.4 filed May 24, 2017. The disclosure of the above application is incorporated herein by reference in its entirety.

FIELD OF THE INVENTION

The present invention relates to a method for detecting corrosion of a surface not exposed to view of a metal piece, wherein radiant thermal energy is directed against the metal piece by illuminating the piece with a pulsed laser beam, so as to cause heating of the metal piece, and wherein the infrared radiation emitted by the metal piece is detected by a thermographic camera, in such a way that corroded portions of said surface are located due to a different thermal response as a function of time of the corroded portions of said surface with respect to non-corroded portions.

PRIOR ART

A method of the above indicated type is for example disclosed in DE 10 2010 023 655 A1. The method known from this document is applied to the detection of corroded portions of the surface of a metal sheet which is not exposed to view, since it is covered by a varnish layer. Also in the case of this known solution, the laser beam is directed against the sheet metal element from the side of the above mentioned surface coated with a varnish layer, any corrosion of this surface being to be detected. Furthermore, the thermographic camera for the thermographic analysis is arranged on the opposite side of the sheet metal element, so that it receives the infrared radiation emitted by the sheet metal element on the side opposite to that from which the laser beam comes.

This known solution necessarily implies that sufficient space is available on both sides of the sheet metal element, in order to arrange the laser device on one side and the thermographic camera on the opposite side.

Furthermore, the need exists of providing methods for thermographic detection of corroded surfaces which enable any corrosion of a sheet element to be detected on the face of the element which is opposite to the face which is exposed to view.

OBJECT OF THE INVENTION

The present invention has the object of providing a new method for detection of any corroded portions of surfaces of metal elements.

The invention aims in particular to providing a method of the above indicated type which can be advantageously used in the automotive industry, for detecting corroded portions of surfaces of components of motor-vehicle structures, or sub-assemblies of motor-vehicle structures, or entire motor-vehicle bodies, on a side which is not exposed to view.

SUMMARY OF THE INVENTION

In view of achieving the above indicated objects, the invention provides a method having the features indicated at the beginning of the present description and further characterized in that:

the beam of laser light is directed against a face exposed to view of a wall of said metal piece, whose opposite face is the surface on which any corrosion must be detected, said thermographic camera is provided on the same side, with respect to said wall, as that where a laser head for emitting said laser beam is provided, said thermographic camera is provided with a processing electronic control system, configured for carrying out a "Lock-in" thermography, detection of corroded portions of said surface is carried out by comparing the response of different surface portions during cooling of the piece, after that illumination with the laser beam has been interrupted.

Studies and tests conducted by the applicant have shown that due to the above mentioned features it is possible to detect with optimal approximation the presence of corroded portions on the face of a wall opposite to the face which is exposed to view and which is illuminated by said laser beam. For example, due to the above mentioned features, the method according to the invention can be advantageously used for locating any corroded portions of the inner surface of hollow components constituted by welded sheet metal elements.

According to a further preferred feature of the present invention, the processing control electronic system with which the thermographic camera is provided is configured for carrying out an approximated evaluation of the wall local thickness L on the basis of the following relation:

$$Q = K * A * \Delta T / L,$$

where Q is the detected thermal energy, K is the thermal coefficient of the material constituting said wall, A is the illuminated area, $\Delta T$ is the difference in temperature between the two sides of the wall, so that an approximated detection of the variation of thickness of said wall due to the corroded surface can be obtained.

DETAILED DESCRIPTION OF THE INVENTION

Figure 2:
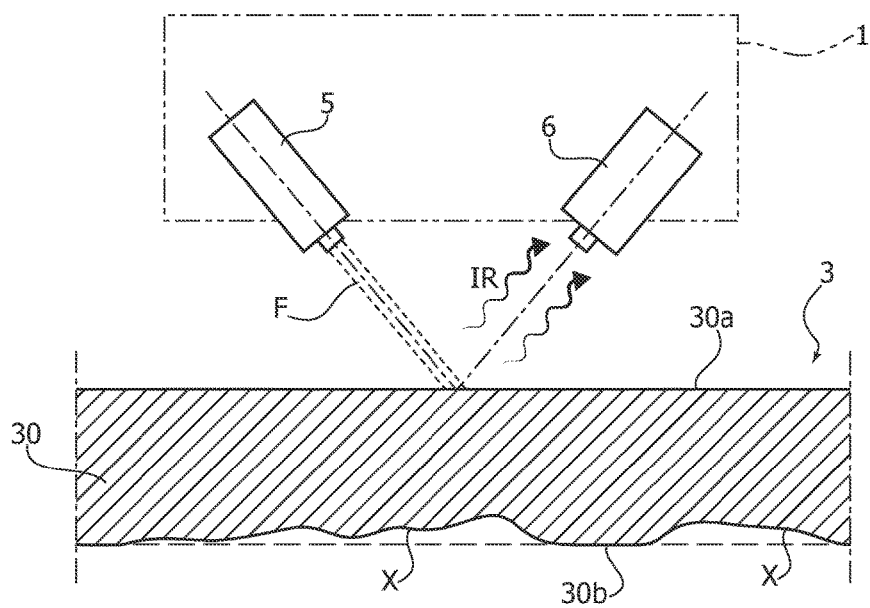
Figure 3:
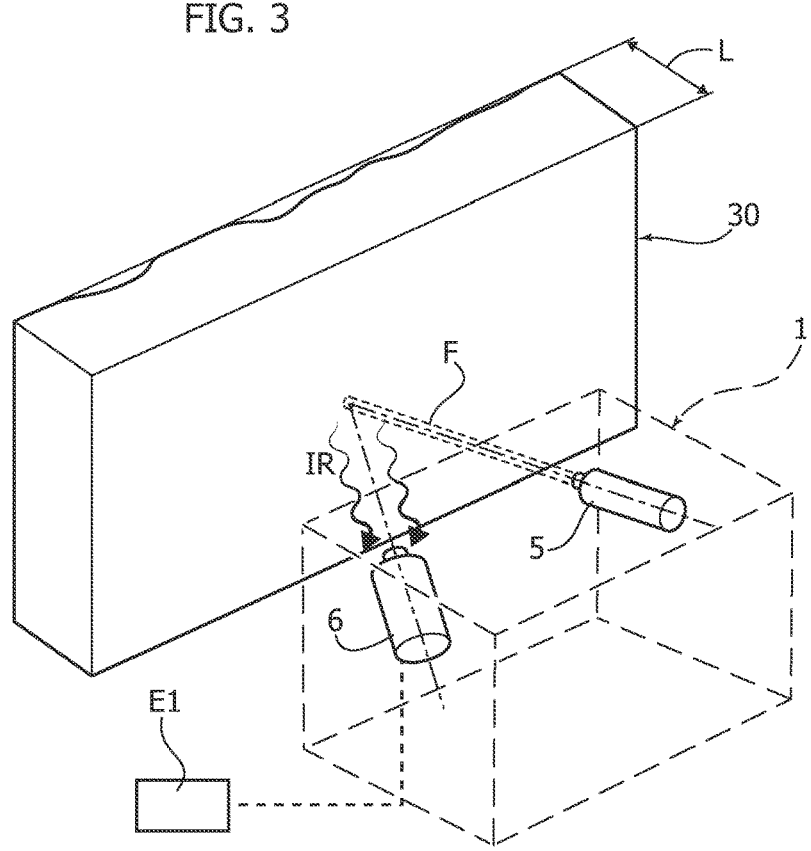
Figure 4:
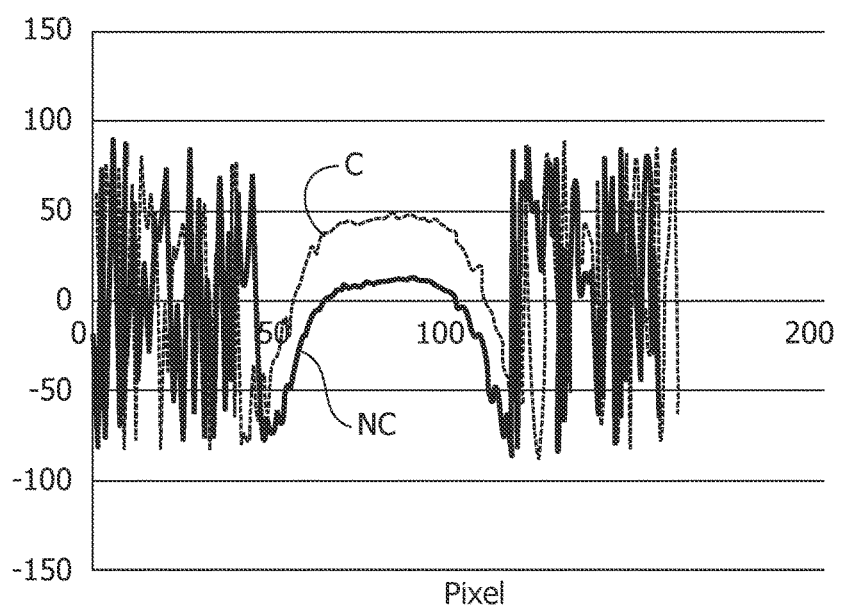

Further features and advantages of the invention will become apparent from the description which follows with reference to the annexed drawings, given purely by way of non limiting example, in which:

FIG. 1 is a diagrammatic view which shows an application of the method according to the invention, in which an instrument for thermographic analysis carried by a robotized arm is used for detecting corroded portions of the inner surface of a hollow metal component, FIG. 2 is a further diagram which shows the principle of operation which is at the basis of the method according to the invention, FIG. 3 is a further perspective diagram corresponding to that of FIG. 2, and FIG. 4 is a diagram which shows the result which can be obtained by the system for thermographic analysis which is used in the present invention.

FIG. 1 shows, by way of example, an application of the method according to the invention in which an instrument 1 for thermographic analysis is carried by a robotized arm 2 of any known type. It is clearly apparent that this embodiment has no limiting value, since the method according to the invention can be carried out by making use of any type of supporting structure for supporting the instrument 1. Also the case in which the instrument is directly carried and operated by an operator is possible.

In the case of the illustrated example, the robotized arm 2 is driven by a respective electronic controller E, which also includes a processing electronic control unit associated with the detection instrument 1. An operator W can control the movements of the robotized arm 2 and the orientation of the detection instrument 1, for example by means of a programming device or tablet T. Also in the case of the illustrated example, the detection instrument 1 is used for detecting any corroded portions of the inner surface of a hollow component 3 of metal material, arranged above a bench 4 inside a work cell C.

As already indicated in the foregoing, this solution is purely given by way of example. The detection instrument 1 can be mounted on a pedestal which can be manually moved by the operator, or could be carried directly by the operator. It is further evident that the method according to the invention can be carried out both in a work cell C as that shown by way of example in FIG. 1, as well as in a production line, or in a workshop in which a motor-vehicle must undergo maintenance or repairing operations.

With reference to FIGS. 2, 3 the detection instrument 1 includes a laser head 5 and a thermographic camera 6 which are therefore arranged on a same side with respect to a wall 30 of the component 3 to be analyzed.

As shown in FIGS. 2, 3, the laser head 5 directs a laser beam F, specifically a pulsed laser beam, against a face 30*a* of the wall 30 which is exposed to view. The opposite face 30*b* of the wall 30, which is hidden from view, is that whose surface may have corroded portions X which can be detected by means of the method of the invention.

As a result of the laser radiation F, wall 30 is heated and emits infrared radiation IR which is detected by the thermographic camera 6. The thermographic camera 6 is connected to a processing electronic control system E1 (FIG. 3) (which in the case of the example of FIG. 1 can also be integrated within controller E) adapted to detect the presence of the corroded portions X of surface 30*b* due to the different response as a function of time of the parts of wall 30 which have the corroded portions X and the parts of wall 30 which do not have corroded portions.

According to the invention, this analysis is specifically conducted during the cooling stage of the metal piece, after that the illumination by the laser beam has been interrupted.

FIG. 4 shows an example of a diagram showing the different thermal response of the corroded portions (line C) and non-corroded portions (line NC) of wall 30. The diagram shows the phase of the thermographic signal for different pixels of the examined area of the wall, along a transverse direction with respect to the optical axis of the thermographic camera.

Studies and tests conducted by the applicant have shown that a relatively precise detection can be obtained by making use of a thermographic camera provided with a processing electronic control system configured for carrying out a "Lock-in" thermography.

"Lock-in" thermography is a method for thermographic analysis which is per se well known to the skilled experts. The basic idea behind Lock-in thermography is that a temperature modulation induced by a heating system having a sinusoidal shape, on the surface of a piece, propagates as a thermal wave. This thermal wave undergoes reflections as any wave, so that the temperature modulation on the surface is modified by the thermal wave which is reflected by the piece. For each pixel, for example by analyzing four images with phase intervals of one quarter of a period, it is possible to calculate the phase offset between the emitted energy and the local thermal response and the maximum amplitude of the periodic thermal signal. Whereas the amplitude image is affected by disomogeneities in absorption by the surface of the infrared emissions and the heating distribution, the phase image is not affected by these disturbances and is therefore more reliable and sensitive. Furthermore, by conducting a phase analysis, the theoretical depth at which a defect can be detected is approximately the double of what is possible with an amplitude analysis.

In the preferred embodiment of the invention, the processing electronic control system E1 is configured to perform an approximated calculation of the local thickness L (FIG. 3) of wall 30 under examination, on the bases of the following relation:

$$Q = K*A*\Delta T/L,$$

where Q is the detected thermal energy, K is the thermal coefficient of the material, A is the affected area and $\Delta T$ is the difference in temperature between the two faces of the wall 30.

In this manner, the detection system can detect variation of thickness of the wall caused by the presence of the corroded portions X on face 30*b*.

As already indicated in the foregoing, the method according to the invention can be advantageously used in the automotive industry, both in a work area as that shown in FIG. 1 of the annexed drawings, or in a production line, or in a workshop in which a motor-vehicle must undergo maintenance or repairing operations. The operator can directly control the detecting instrument 1 by manually positioning the instrument adjacent to the component to be examined, or he may make use of any supporting structure or other equipment (such for instance also a robotized arm) for controlling the position of the detection instrument 1 with respect to the piece. It is not even excluded the possibility to hold the detection instrument at a fixed position and moving the piece with respect to the instrument, in order to examine different portions of the piece.

Contrary to known solutions, the method according to the invention performs a detection of the corrosion of a face hidden to view of a wall of the metal piece to be examined, whose opposite face is illuminated by a pulsed laser beam. The detection instrument includes both the laser head 5 and the thermographic camera 6, which therefore are both arranged on a same side with respect to the analyzed wall.

Naturally, while the principle of the invention remains the same, the details of construction and the embodiments may widely vary with respect to what has been described and illustrated purely by way of example, without departing from the scope of the present invention.

What is claimed is:

1. A method for detecting corrosion of a surface not exposed to view of a metal piece, wherein radiant thermal energy is directed against the metal piece, by illumination with a pulsed laser beam, so as to cause heating of said metal piece, the method comprising:
    directing the illumination with the pulsed laser beam against a face exposed to view of a wall of said metal piece, whose opposite face is the surface not exposed to view on which corrosion must be detected,
    providing a thermographic camera on a same side, with respect to said wall, where a laser head for emitting said pulsed laser beam is provided, wherein infrared radiation emitted by the metal piece is detected by the thermographic camera, providing said thermographic camera with a processing electronic control system, configured for performing a "Lock-in" thermography, performing detection of corroded portions of said surface by comparing a thermal response as a function of time of different surface portions during cooling of the metal piece, after illumination with the laser beam has been interrupted, so that the corroded portions of said surface not exposed to view are located due to a different thermal response as a function of time with respect to non-corroded portions.

2. The method according to claim 1, wherein said processing electronic control system is programmed for performing an approximated calculation of a variation of a thickness of the wall under examination on the basis of the following relation:

$$Q = K * A * \Delta T / L,$$

wherein Q is detected thermal energy, K is a thermal coefficient of the material constituting said wall, A is an affected area, and ΔT is a difference in temperature between the two faces of said wall, so as to obtain an approximated detection of the variation of thickness of said wall due to a presence of corroded surface portions.

* * * * *